(12) United States Patent
Rush

(10) Patent No.: US 7,399,401 B2
(45) Date of Patent: Jul. 15, 2008

(54) METHODS FOR USE IN ASSESSING A FLOW CONDITION OF A FLUID

(75) Inventor: Benjamin M. Rush, Oakland, CA (US)

(73) Assignee: Abbott Diabetes Care, Inc., Alameda, CA (US)

( * ) Notice: Subject to any disclaimer, the term of this patent is extended or adjusted under 35 U.S.C. 154(b) by 97 days.

(21) Appl. No.: 11/106,256

(22) Filed: Apr. 13, 2005

(65) Prior Publication Data
US 2005/0249606 A1 Nov. 10, 2005

Related U.S. Application Data

(63) Continuation-in-part of application No. 10/683,659, filed on Oct. 9, 2003, now Pat. No. 6,916,159.

(60) Provisional application No. 60/424,613, filed on Nov. 6, 2002, provisional application No. 60/417,464, filed on Oct. 9, 2002.

(51) Int. Cl.
*G01N 27/26* (2006.01)

(52) U.S. Cl. ............... 205/789.5; 204/400; 204/403.01; 204/409; 73/861.08; 205/775

(58) Field of Classification Search ................. 204/400, 204/403.01, 409, 411; 205/775, 789.5, 793.5; 73/861.07, 861.08; 600/504
See application file for complete search history.

(56) References Cited

U.S. PATENT DOCUMENTS 3,750,687 A * 8/1973 Williams ..................... 137/1
3,930,493 A 1/1976 Williamson
4,018,547 A 4/1977 Rogen (Continued)

FOREIGN PATENT DOCUMENTS

WO WO 2004/028337 A2 4/2004

(Continued)

OTHER PUBLICATIONS

Barbosa et al, Analyst, 121, pp. 1789-1793, Dec. 1996.*

(Continued)

*Primary Examiner*—Kaj K Olsen
(74) *Attorney, Agent, or Firm*—Jackson & Co., LLP

(57) ABSTRACT

A device for use in assessing a flow condition of a fluid, or a fluid in a flow path, is provided. The device comprises at least one electrochemical cell, comprising a working electrode and at least one other electrode, sufficient for communication with the fluid, or sufficient for communication with a flow path, such that when sufficient fluid is in the flow path, the cell is in communication with the fluid. The fluid comprises a component sufficient to affect a mass-transport limited electrochemical reaction at the working electrode. The device also comprises at least one microcontroller operably connected to the at least one electrochemical cell for providing a potential or a current to the working electrode and for assessing the electrochemical reaction. A method of assessing a flow condition of a fluid, or a fluid in a flow path, is also provided. The device and the method of the present invention may be used in connection with the delivery of a fluid-borne or fluidized drug or medicament to a subject.

64 Claims, 8 Drawing Sheets

U.S. PATENT DOCUMENTS

| | | | |
|---|---|---|---|
| 4,439,197 | A | 3/1984 | Honda et al. |
| 4,570,492 | A * | 2/1986 | Walsh ................... 73/861.05 |
| 4,736,748 | A * | 4/1988 | Nakamura et al. .......... 600/352 |
| 4,984,581 | A | 1/1991 | Stice |
| 5,012,667 | A * | 5/1991 | Kruse ........................ 73/1.34 |
| 5,079,920 | A | 1/1992 | Whitehead et al. |
| 5,207,666 | A | 5/1993 | Idriss et al. |
| 5,211,371 | A | 5/1993 | Coffee |
| 5,211,626 | A | 5/1993 | Frank et al. |
| 5,366,292 | A | 11/1994 | Voss |
| 5,382,331 | A * | 1/1995 | Banks ........................ 205/781 |
| 5,575,770 | A | 11/1996 | Melsky et al. |
| 5,622,413 | A | 4/1997 | Kim et al. |
| 5,622,482 | A | 4/1997 | Lee |
| 5,848,990 | A | 12/1998 | Cirelli et al. |
| 6,041,665 | A * | 3/2000 | Hussain ................ 73/861.357 |
| 6,059,546 | A | 5/2000 | Brenan et al. |
| 6,085,871 | A | 7/2000 | Karamata |
| 6,162,202 | A | 12/2000 | Sicurelli et al. |
| 6,368,274 | B1 | 4/2002 | Van Antwerp et al. |
| 6,375,638 | B2 | 4/2002 | Nason et al. |
| 6,425,829 | B1 | 7/2002 | Julien |
| 6,471,980 | B2 | 10/2002 | Sirhan et al. |
| 6,582,393 | B2 | 6/2003 | Sage, Jr. |
| 6,669,669 | B2 | 12/2003 | Flaherty et al. |
| 6,692,457 | B2 | 2/2004 | Flaherty |
| 6,723,072 | B2 | 4/2004 | Flaherty et al. |
| 2002/0118090 | A1 | 8/2002 | Park et al. |
| 2003/0078560 | A1 | 4/2003 | Miller et al. |
| 2003/0198558 | A1 | 10/2003 | Nason et al. |
| 2004/0019321 | A1 | 1/2004 | Sage et al. |
| 2004/0064133 | A1 | 4/2004 | Miller et al |
| 2005/0235732 | A1 | 10/2005 | Rush et al. |
| 2005/0238503 | A1 | 10/2005 | Rush et al. |

FOREIGN PATENT DOCUMENTS

| | | |
|---|---|---|
| WO | WO 2006/110913 A2 | 10/2006 |
| WO | WO 2006/113408 A2 | 10/2006 |
| WO | WO 2006/113521 A2 | 10/2006 |

OTHER PUBLICATIONS

Bard and Faulkner, Electrochemical Methods, 2nd Ed., pp. 28-35, 2001.*

Ursino et al, IEEE Transactions on Biomedical Engineering, 36(2), pp. 183-191, Feb. 1989.*

Notification of Transmittal of the International Search Report or the Declaration, mailed Apr. 1, 2004, in International Application No. PCT/US03/32191 of TheraSense, Inc.

"An Electrochemical Slow Flow Meter," http://gore.ocean.washington.edu/research/slow_flow_meter.html, Feb. 10, 2005, 3 pages.

Bard et al., "Methods Involving Forced Convection-Hydrodynamic Methods,"*Electrochemical Methods—Fundamentals and Applications*, Second Edition, 2001, pp. 331-367.

"Notification of the Transmittal of the International Search Report and the Written Opinion of the International Searching Authority, or the Declaration", for PCT Application No. PCT/US06/14281, dated Feb. 22, 2007, 12 pages.

Caplus abstract for Barbosa et al., "Electrochemical Studies of Zinc in Zinc-Insulin Solution," Analyst., 121(12), pp. 1789-1793, 1996.

* cited by examiner

METHODS FOR USE IN ASSESSING A FLOW CONDITION OF A FLUID

CROSS REFERENCE TO RELATED APPLICATIONS

The present application is a continuation-in-part of U.S. application Ser. No. 10/683,659 of Benjamin M. Rush et al., filed on Oct. 9, 2003, and issued as U.S. Pat. No. 6,916,159 on Jul. 12, 2005, which is related to and claims priority based on U.S. Provisional Application No. 60/417,464, entitled "Disposable Pump for Drug Delivery System," filed on Oct. 9, 2002, and U.S. Provisional Application No. 60/424,613, entitled "Disposable Pump and Actuation Circuit for Drug Delivery System," filed on Nov. 6, 2002, each of which is hereby incorporated herein, in its entirety, by this reference. The parent application, U.S. application Ser. No. 10/683,659, was published as U.S. Patent Application Publication No. 2004/0115067 A1. The present application is related to U.S. application No. 11/106,155 of Benjamin Rush et al., entitled "Variable Volume, Shape Memory Actuated Insulin Dispensing Pump," published as U.S. Patent Application Publication No. 2005/0238503 A1, and U.S. application Ser. No. 11/105,711 of Benjamin M. Rush, entitled "Fluid Delivery Device with Autocalibration," published as U.S. Patent Application Publication no. 2005/0235732 A1, each of which is filed concurrently with the present application and is hereby incorporated herein, in its entirety, by this reference.

FIELD OF THE INVENTION

This invention generally relates to a device and a method for assessing flow of a fluid. The device and method may be used in connection with fluid delivery devices, systems, and methods. Merely by way of example, the device and method may be used in connection with a small volume, disposable medical device for the precision delivery of a medicine or a drug, such as insulin, and associated systems and methods.

BACKGROUND OF THE INVENTION

A wide variety of fluid delivery devices have been developed for various applications, such as the delivery of medicine or drugs. By way of example, automated infusion devices that can deliver a fluidized or fluid-borne drug to a subject with extremely high precision have been developed. (See, for example, the above-referenced U.S. Patent Application Publication No. 2004/0115067 A1 and the above-referenced U.S. Patent Application Publication No. 2005/0238503 A1 of Benjamin Rush et al, concurrently filed herewith.) If these devices fail to deliver a drug to a subject at an acceptable or intended rate, the consequences can be anywhere from relatively minor to relatively major, even deadly. Thus, some means of verifying that a drug is being delivered or has been delivered at an acceptable or intended rate is typically incorporated into automated drug infusion devices.

Drug delivery verification means may allow for the detection of insufficient and/or excessive drug delivery or fluid flow. Traditional means or methods for measuring fluid flow include hot-wire anemometry, generation and detection of a heat pulse, injection and detection of a tracer component, and electromagnetic flow measurement, such as via passage of an ion-containing liquid through a loop and detection of an associated current.

Other means for measuring fluid flow have been developed for specific devices, as well. For example, means for detecting a build-up of pressure within a drug delivery path, such as that caused by a blockage in the path, have been incorporated into portable insulin pumps. These means, which include a pressure transducer, can detect insufficient fluid flow from the insulin pump, such as insufficient flow caused by a blockage in the delivery tubing or in the cannula, but cannot detect excessive fluid flow from the pump. The pressure transducer adds to the cost and complexity of this portable insulin pump.

Another method of detecting insufficient fluid flow from a fluid delivery device, such as a drug delivery device, has been disclosed. (See U.S. Pat. No. 6,692,457.) According to this method, the fluid flows past a resilient chamber, such as a balloon or a bubble, in the flow path. If the flow path is blocked at a point downstream from the bubble, for example, the pressure in the flow path increases, such that the bubble expands and a surface of the expanded bubble activates a sensor to indicate a blockage condition.

Methods of monitoring the rate of fluid delivery from a drug delivery device have also been disclosed. (See U.S. Pat. No. 6,582,393 and U.S. Patent Application Publication No. 2004/0019321 A1.) According to one such method, a small amount of fluid is heated via a heating element, such as a laser, and the presence of this heated amount of fluid is detected downstream via a heat sensor, such as another laser, and a rate of fluid flow is determined and evaluated. According to another such method, the flowing fluid is subjected to a magnetic field, such that ions in the fluid produce a directional current, which is then detected and associated with the volumetric flow rate. Compensating adjustments to the flow rate may then be made accordingly.

Devices for measuring fluid flow have also been developed for applications unrelated to drug delivery. By way of example, a device for measuring the very slow flow associated with hydrothermal systems, such as hydrothermal systems on the seafloor or dilute hydrothermal systems, has been described at http://gore.ocean.washington.edu/ research/ slow_flow_meter.html. In the case of seawater, the seawater fluid enters the tubular device and generates a "puff" of chlorine gas at a platinum electrode of an electrode pair within the device, via the electrochemical reaction, $2Cl^- \rightarrow Cl_2 + 2e^{31}$. The puff is confined within the device, where it is detected via two sensing electrodes placed at fixed distances from the platinum electrode along the tubular device. The times required for the puff to travel known distances along the device provide a measure of the flow velocity of the seawater.

Devices for measuring various parameters of a moving fluid have also been developed for various applications. By way of example, a rotating disk electrode has been developed as a means of producing a very regular and reproducible liquid flow profile when immersed in a liquid. If the liquid contains a dilute species that can react at the electrode, the rate of reaction will depend on the speed of rotation associated with the rotating disk electrode. This phenomenon may be used to determine the concentration of the dilute species in the liquid. (See, for example, A. J. Bard and L. R. Faulkner, *Electrochemical Methods*, 2nd Ed., John Wiley (2001).)

Further development of fluid flow measurement devices, and associated systems, devices and methods, is desirable.

BRIEF SUMMARY OF THE INVENTION

According to an aspect of the present invention, a technique for assessing, measuring, and/or monitoring flow of a medium is provided. The flow of the medium may be relatively unconfined or natural, such as the flow of water in a body of water, such as sea or ocean water in a body thereof, or may be in a flow path, such as the flow of insulin from an insulin pump through a delivery channel, for example. An electrochemical cell is immersed in the medium and is used to assess, measure, and/or monitor the state of flow of the medium. According to an aspect of the invention, the cell is used to assess, measure, and/or monitor the rate of an electrochemical reaction associated with the medium. According to an aspect of the invention, a device for carrying out the technique is provided. The device may be a simple, inexpensive, qualitative and/or quantitative device.

According to an aspect of the invention, the technique is based on the notion of a mass-transport limited reaction. The rate at which a chemical reaction proceeds is determined by at least one of two things, the inherent kinetics of the reaction or the rate at which reactants become available to react. Examples of the latter include heterogeneous reactions, such as those that take place at a catalytic or reacting phase boundary. By way of example, an oxidation reaction in which ferrous ion in water is oxidized to ferric ion ($Fe^{2+} \rightarrow Fe^{3+} + e^-$) at an appropriate working electrode, such as a gold working electrode at an appropriate potential, for example, is such a reaction. Further by way of example, a reduction reaction in which ferric ion in water is reduced to ferrous ion ($Fe^{3+} + e^- \rightarrow Fe^{2+}$) at an appropriate working electrode, such as a gold working electrode at an appropriate potential, for example, is such a reaction. In either an oxidation reaction or a reduction reaction, if the reactant were readily available without limitation, the reaction would proceed at a rate dictated by the inherent reaction kinetics of the reaction. However, if the reactant were not so readily available, such as in the case where the concentration of the reactant is sufficiently low so that the rate at which it diffuses to the working electrode surface is slower that the rate at which it reacts at the working electrode surface, then the rate of reaction would be dictated by the transport rate of the reactant, rather than by the inherent reaction kinetics of the reaction. Thus, increasing the rate of mass transport of the reactant, such as via water movement (for example, via forced flow or circulation of water), would increase the rate of such a reaction. Accordingly, the rate of a mass-transport limited reaction may serve as an indicator as to the status or condition of fluid flow.

According to an aspect of the present invention, the rate of a mass-transport limited reaction, such as the oxidation reaction or the reduction reaction just described, serves as a measure or monitor of the state of the fluid flow around it. According to another aspect of the present invention, a device and a method for assessing, measuring, and/or monitoring the flow of fluid based on the principle just described, is provided. According to yet another aspect of the present invention, a device and a method for assessing, measuring, and/or monitoring the flow of a drug or a medicament, such as insulin, for example, that is pumped through a flow channel, such as via an automatic infusion pump, for example, is provided. According to yet another aspect of the present invention, a device and a method for assessing a flow condition of a fluid, may be used to provide information concerning any of a wide variety of flow conditions and parameters, may be used to indicate or provide notification of a deviation from a desirable or an intended flow condition, may be used in a feedback loop to control, adjust, or maintain the flow condition, such as an automated feedback loop, for example, and/or the like.

These and various other aspects, features and embodiments of the present invention are further described herein.

BRIEF DESCRIPTION OF THE DRAWINGS

A detailed description of various aspects, features and embodiments of the present invention is provided herein with reference to the accompanying drawings, which are briefly described below. The drawings are illustrative and are not necessarily drawn to scale. The drawings illustrate various aspects or features of the present invention and may illustrate one or more embodiment(s) or example(s) of the present invention in whole or in part. A reference numeral, letter, and/or symbol that is used in one drawing to refer to a particular element or feature may be used in another drawing to refer to a like element or feature.

DETAILED DESCRIPTION OF THE INVENTION

Figure 1:
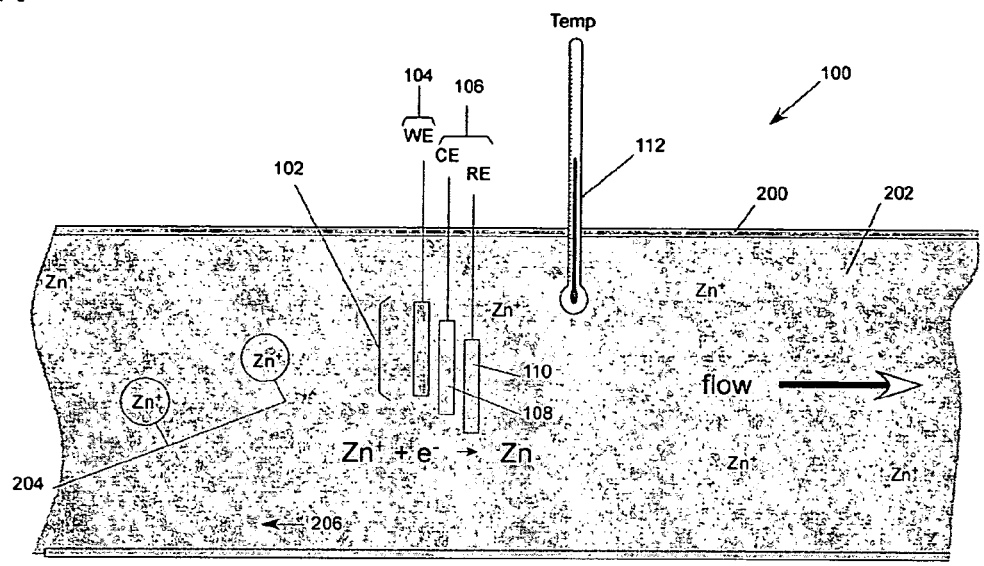
FIG. 1 (FIG. 1) is a schematic illustration of a device according to an embodiment of the present invention.

In the description of the invention herein, it will be understood that a word appearing in the singular encompasses its plural counterpart, and a word appearing in the plural encompasses its singular counterpart, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise. Still further, it will be understood that any figure or number presented herein in connection with the invention is approximate, and that any numerical range includes the minimum number and the maximum number defining the range, unless implicitly or explicitly understood or stated otherwise.

Various terms are generally described below to facilitate an understanding of the invention. It will be understood that a corresponding description of these various terms applies to corresponding linguistic or grammatical variations or forms of these various terms. It will also be understood that the general description of any term below may not apply or may not fully apply when the term is used in a non-general or more specific manner. It will also be understood that the invention is not limited to the terminology used herein, or the descriptions thereof, for the description of particular embodiments. It will further be understood that the invention is not limited to embodiments of the invention as described herein or applications of the invention as described herein, as such may vary.

The term "amperometry" generally refers to the determination or measurement of the strength of a current and encompasses steady-state amperometry, chronoamperometry, and Cottrell-type determination or measurement.

The term "concentration" may generally refer to a signal that is indicative of a concentration of a component in a medium, such as a current signal or a voltage signal, for example, to a more typical indication of a concentration of a component in a medium, such as mass of the component per unit volume of the medium, for example, and/or the like.

The term "control" generally refers to any type of control and encompasses the maintenance of a condition or status and the adjustment of a condition or status, which control may be automated. In various embodiments of the present invention, a microcontroller sufficient to control a delivery of a fluid or a fluid delivery device based on any of a variety of parameters, such as a current, a potential, a charge, a resistance, a rate of an electrochemical reaction, a fluid flow rate, a fluid temperature, and/or the like, is provided. The microcontroller may be sufficient to control such delivery in an automated manner, such as via a feedback loop.

The term "coulometry" generally refers to the determination of charge passed or projected to pass during complete or nearly complete electrolysis of a material, either directly on the electrode or via at least one electron-transfer agent. The charge is determined by measurement of electrical charge passed during partial or nearly complete electrolysis of the material, or, more often, by multiple measurements during the electrolysis associated with a decaying current over an elapsed period. The decaying current results from the decline in the concentration of the electrolyzed species caused by the electrolysis.

A "counter electrode" generally refers to at least one electrode that is paired with a working electrode and through which passes an electrochemical current. In general, the counter electrode is a conductor that completes the electrochemical cell or circuit. The current that flows into the electrically conductive solution via the working electrode leaves the solution via the counter electrode. The term "counter electrode" encompasses a counter electrode that also functions as reference electrode (i.e., a counter/reference electrode), unless the description provides that a "counter electrode" excludes a counter/reference electrode.

The term "current" generally refers to one type of measure that can be used in connection with the present invention. It will be understood that although current is often discussed as a type of measure employed herein, current, potential or voltage, charge, or resistance may be employed alone or in any suitable combination as a type of measure herein.

The term "electroactive" generally refers to a species in solution that can take part in an electrochemical reaction or that can be adsorbed on the working electrode.

The term "electrochemical cell" generally refers to a cell at which an electrochemical reaction may take place. In a potentiostatic mode, a working electrode of such a cell may be controlled or held at a certain potential or voltage and may produce a current, which may be measured. In a galvanistatic mode, a working electrode of such a cell may be controlled or held at a certain current and produce a voltage, which may be measured. In yet another mode, current, voltage, charge, and/or resistance associated with such a cell, or with simply an electrode pair (i.e., a pair of electrodes, neither of which is a reference electrode, such that an electrochemical reaction at the pair may be uncontrolled or undefined), may be measured, such as may be useful to determine whether or not an electrochemical reaction is taking place at the working electrode. In connection with an electrochemical cell, any of these modes may be quantitatively or qualitatively employed. In connection with a pair of electrodes, the latter mode is generally qualitatively employed.

The term "electrolysis" generally refers to the electrooxidation or electroreduction of a compound either directly at an electrode or via at least one electron-transfer agent, such as a redox mediator and/or an enzyme, for example. Examples of electrolysis via an electron-transfer agent and/or an enzyme are provided in U.S. Pat. Nos. 6,676,816, 6,605,200, 6,605, 201, and 7,052,591 and U.S. Patent Application Publication Nos. 2005/0173245 A1 and 2005/0215871 A1, for example.

The term "flow path" generally refers to any path, pattern, direction, way, manner, and/or the like, in which fluid may flow. The flow path may be natural or unnatural, introduced, relatively unconfined or relatively confined, anything in between, the like, or any combination thereof, merely by way of example. The term "flow path" encompasses a flow path of a fluid in a body of fluid, such as the flow of water, ocean water, or sea water, in a body of fluid, whether a natural flow, such as via a natural current, or an artificially introduced flow, such as via artificial movement or agitation of the fluid, or the flow path of a fluid in a flow channel, such as a delivery channel from a source of fluid, which may be naturally fed, gravity fed, pump fed, and/or the like, merely by way of example.

The term "fluid" generally refers to any medium that can support an electrochemical reaction at an electrochemical cell within the fluid. In most cases, the term "medium" generally refers to a liquid medium. The medium should be sufficiently ion conductive to support an electrochemical reaction at the electrochemical cell. For example, when the electrochemical reactant is dilute, such as dilute ionic zinc in an insulin preparation, the fluid may contain an inert ionic species or a supporting electrolytic component that is sufficient to support the electrochemical reaction at the electrochemical cell. A supporting electrolyte is one that is added to a solution for the purpose, such as the sole or predominant purpose, for example, of increasing the conductivity of the solution and that does not participate in the electrochemical reaction. Such a supporting electrolyte may be referred to as an "inert" electrolyte, an "indifferent" electrolyte, or a "swamping" electrolyte. Sodium chloride and potassium are examples of supporting electrolytes, merely by way of example. A supporting electrolyte may be present in an amount of about 0.1 M to about 1.0 M relative to the solution, merely by way of example, and any suitable supporting electrolyte or combination of supporting electrolytes may be used.

An "implantable" device generally refers to a fully implantable device that is implanted fully within a body and/or an at least partially implantable device that is at least partially implanted within a body. An example of an at least partially implantable sensing device is a transcutaneous sensing device, sometimes referred to as a subcutaneous sensing device, that is associated with a portion that lies outside of a body and a portion that penetrates the skin from the outside of the body and thereby enters the inside of the body. The sensing device may be a continuous or in vivo analyte-sensing device that may be used to sense an analyte, such as glucose, in the body or a portion thereof, merely by way of example.

The term "measure," as in "to measure the concentration," is used herein in its ordinary sense and generally refers to the act of obtaining an indicator, such as a signal, that may be associated with a value, such as concentration, for example, and to the act of ascertaining a value, such as a concentration, for example. The term "monitor," as in "to monitor the concentration," refers to the act of keeping track of more than one measurement over time, which may be carried out on a systematic, regular, substantially continuous, and/or on-going basis. The term "assess" encompasses the terms measure and monitor. The terms assess, measure, and monitor may be used generally herein, such as alternately, alternatively, or interchangeably, or more specifically, as just described.

The term "measurement" may generally refer to a signal that is indicative of a concentration of an analyte in a medium, such as a current signal or a voltage signal, for example, to a more typical indication of a concentration of an analyte in a medium, such as mass of the analyte per unit volume of the medium, for example, or the like. The term "value" may sometimes be used herein as a term that encompasses the term "measurement."

The term "patient" generally refers to a living animal, and thus encompasses a living mammal and a living human, for example. The term "subject" may sometimes be used herein as a term that encompasses the term "patient" and/or the term "user."

A "reference electrode" generally refers to at least one electrode that is used as a reference against which the working electrode potential is assessed or measured. The reference electrode may be, and ideally is, non-polarizable, or has a constant and known electrode potential even if current flows through it. The term "reference electrode" encompasses a reference electrode that also functions as a counter electrode (i.e., a counter/reference electrode), unless the description provides that a "reference electrode" excludes a counter/reference electrode.

The term "working electrode" generally refers to at least one electrode at which a material is electrooxidized or electroreduced. Generally, in a potentiostatic mode, the working electrode is the electrode at which the potential is controlled and the current is measured, and in a galvanistatic mode, the working electrode is the electrode at which the current is controlled and the potential or voltage is measured.

According to the present invention, a device and a method for use in assessing a flow condition of a fluid are provided. The device 100 comprises an electrochemical cell 102, which comprises a working electrode (WE) 104 and at least one other electrode 106, as shown in FIG. 1. The at least one other electrode 106 may comprise a counter/reference electrode (not shown), which may be encompassed by the term counter electrode or reference electrode, as indicated previously, or a counter electrode (CE) 108 and a reference electrode (RE) 110, as shown in FIG. 1. Independently, each of the working electrode 104 and the counter electrode 108 comprises a material that is an electrical conductor and may be selected from the group consisting of carbon, gold, silver, platinum, copper, a conductive polymer, and any combination thereof, merely by way of example. The reference electrode 110 may be any of the following types, namely, an Ag/AgCl electrode, an Hg/HgO, an $Hg/Hg_2SO_4$ electrode, an $Hg/Hg_2Cl_2$ electrode, a normal hydrogen electrode, and a reversible hydrogen electrode, merely by way of example. Each of the electrodes of the electrochemical cell may be comprised of any suitable material or any suitable combination of materials. Generally, any suitable electrodes for the electrochemical cell 102 may be used and any selection of same may be based on the nature of the electrochemical reaction that is to take place at the electrochemical cell 102 and any condition that may affect that electrochemical reaction.

The electrochemical cell 102 is sufficient for communication with the fluid 202. Merely by way of example, when the fluid is in a flow path 200, the electrochemical cell 102 is sufficient for communication with the fluid path 200, such that when sufficient fluid 202 is in the flow path 200, the cell 102 is in communication with the fluid. The device 100 may be independent of the flow path 200 and/or of a source (not shown) of the fluid. Merely by way of example, the device may be adapted for use with an existing flow path, such as an outlet of a fluid delivery device or pump that is in communication with a source of fluid or has its own supply of fluid, or a natural flow path that is in communication with a source of fluid or has its own supply of fluid, such as a blood vessel, for example. Such an adaptation may comprise putting the electrochemical cell into communication with the existing flow path, such as introducing the electrochemical cell into the flow path, preferably in a manner that substantially avoids the leakage of fluid from the flow path in the vicinity of the cell components. Alternatively, the device may itself comprise a flow path and/or a source of the fluid.

A device 100 according to the present invention may comprise one electrochemical cell 102, as described above and shown in FIGS. 1 and 2, or two or more electrochemical cells (not shown). Multiple electrochemical cells may be located in the same general vicinity relative to the flow path 200, or at different locations relative to the flow path 200. Multiple electrochemical cells may be used for redundant assessment, measurement, and/or monitoring of the flow condition of the fluid 202 in the flow path 200.

Figure 2:
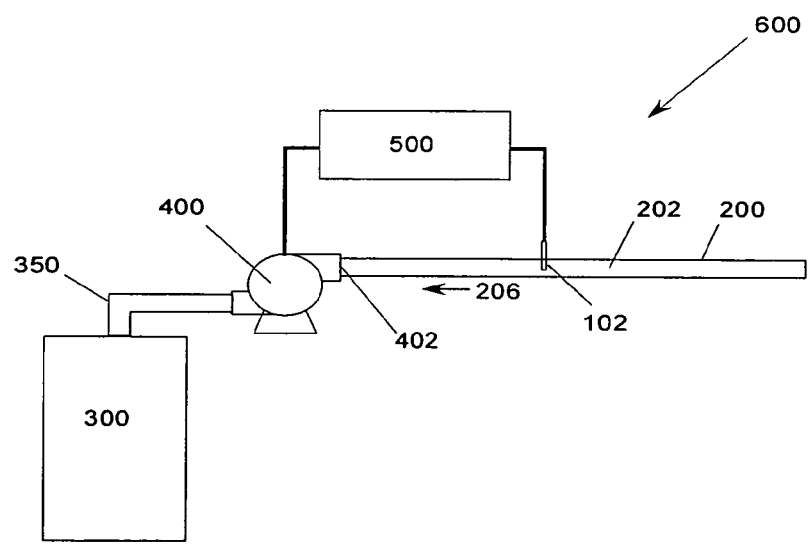
FIG. 2 (FIG. 2) is a schematic illustration of a device according to an embodiment of the present invention.

According to an embodiment of the present invention, the device 100 may be used in connection with an existing source of fluid and an existing fluid delivery device or pump, as described above and as will be understood with reference to FIG. 2. According to another embodiment of the present invention, a device 600 may comprise a source of fluid 300, such as a fluid reservoir 300, and a fluid delivery device 400, such as a pump 400, in communication, such as via a conduit 350, as shown in FIG. 2. The fluid delivery device or pump 400 is in communication with the flow path 200 for the delivery of fluid 202 thereto, as shown in FIG. 2. In such a case, the flow path 200 is in communication with the outlet 402 of the fluid delivery device or pump 400.

The pump 400 may be one sufficient for delivering the fluid in a continuous manner, or in a non-continuous manner, such as in two or more pulses, or two or more periodic discrete pulses. It will be understood that appropriate pump parameters may vary according to the fluid to be pumped and the application of that fluid. Merely by way of example, in the case of the delivery of a fluid that comprises a drug, a medicament, a nutrient, a dietary or health supplement, any source thereof, any combination thereof, and/or the like, to a subject, such parameters may vary according to the drug, medicament, nutrient, or supplement, etc., the characteristics of the subject, the characteristics of the condition the drug, medicament, nutrient, or supplement, etc., is intended to address, and/or the like, all of which may be highly variable. It will be appreciated that via a fluid, a wide variety of drugs or medicaments may be delivered to a subject, such as an antibiotic, a nutritional fluid, a dietary supplement, a health supplement, total parenteral nutrition (TPN), an analgesic, an anesthetic, a pain reliever, such as morphine, for example, a hormone, a hormonal drug, a gene therapy drug, an anticoagulant, a cardiovascular drug, AZT, a chemotherapeutic drug, any source thereof, and any combination thereof, merely by way of example.

Merely by way of example, the pump 400 may comprise a micro-pump sufficient for the delivery of fluid in small quantities, such as from about 1 to about 10,000 microliters (µL) per day, or from about 100 to about 1000 µL per day or around 400 µL per day on average, as may be suitable for the delivery of insulin to a diabetic person. The pump 400 may comprise a micro-pump sufficient for the delivery of fluid in periodic pulses, such as from about 0.1 to about 10 µL per pulse or from or from about 0.5 to about 1 µL per pulse, as may be suitable for the delivery of insulin to a diabetic person. Suitable pulse periods and repetition rates are quite variable depending on the application. By way of example, the fluid may be delivered at a rate of from about every second for a fast multi-dose bolus to about every 10 minutes for a slow basal rate, as may be suitable for the delivery of insulin to a diabetic person.

Preferably, the pump is a micro-pump when the fluid to be delivered is a drug or a medicament for a subject, such as insulin for a diabetic subject. In general, a device of the present invention may be run by a relatively modest battery or other power source (see FIG. 7, for example), such as a very small 357 silver oxide battery that has a lifetime of about a few weeks, as the power consumption of the device is very low. Merely by way of example, in a device of the present invention that is used in connection with a micro-pump (see FIG. 7, for example), the power consumption may be relatively minor, trivial, or negligible relative to that of the micro-pump, particularly in the case of a small micro-pump that is worn on a subject, such as via patch disposed on the subject's skin, and delivers a drug or medicament to the subject.

The fluid 202 is sufficient to support an electrochemical reaction at the working electrode 104 of an electrochemical cell 102 that is in communication with the fluid. The fluid comprises a component 204 (FIG. 1) sufficient to the electrochemical reaction such that it is mass-transport limited. Upstream of the electrochemical cell 102, as generally indicated by the arrow 206 (FIGS. 1 and 2), the fluid arid the component may be integral, or the fluid may comprise the component and a substituent that is free of the component. Merely by way of example, at that upstream point, the fluid may comprise an insulin preparation that comprises an electroactive component, such as ionic zinc ($Zn^+$), for example, or the fluid may comprise an electroactive component and a substituent, such as an insulin preparation, that is free of an electroactive component.

The component 204 of the fluid 202 may be sufficient to participate in, promote, or interfere with an electrochemical reaction at the working electrode 104, where participating encompasses reacting, promoting encompasses catalyzing, and interfering encompasses inhibiting and suppressing. The component may be sufficient to change the rate of an electrochemical reaction at the working electrode 104 from what it would be were the component absent. The component of the fluid may be relatively dilute in concentration, such as from about $10^{-7}$ M to about $10^{-2}$ M, merely by way of example, as may be the case for an electroactive component of ionic zinc in an insulin preparation, for example.

Merely by way of example, the component 204 of the fluid 202 may be electroactive. Such an electroactive component may comprise an ionic species, a metallic species, a metal-oxide species, an organic species, oxygen, water, any source thereof, and any combination thereof. By way of example, such an electroactive component may comprise any suitable material from a complete table of standard electrode potentials, such as any of a variety of metals, metal ions, metal oxides, and any combination thereof. (See, for example, A. J. Bard and L. R. Faulkner, *Electrochemical Methods*, $2^{nd}$ Ed., John Wiley (2001), Appendix C.) Further by way of example, such an electroactive component may comprise any suitable organic material or compound, such as glucose for use in connection with a working electrode that comprises a glucose oxidase enzyme, may be used. An example of a fluid 202 that comprises an electroactive component 204 is insulin preparation that comprises the drug insulin, which is not electroactive, and an electroactive component, such as an ionic species, such as ionic zinc, for example. The electroactive component may participate in the electrochemical reaction at the working electrode 104 of the electrochemical cell 102. The electroactive component may be sufficiently dilute relative to the fluid, such that the electrochemical reaction is mass-transport limited.

Further, merely by way of example, the component 204 of the fluid 202 may comprise a gas, such as air, which may be in the form of at least one gas bubble, such as an air bubble, which interferes with an electrochemical reaction by interfering with the transport of an electrochemical reactant toward the working electrode 104. For example, as mentioned above, the fluid, such as an insulin preparation described above, may comprise an ionic species, such as ionic zinc, that participates in the electrochemical reaction at the working electrode, and an air bubble component of the fluid may interfere with transport of the ionic species to the working electrode. Further, merely by way of example, the fluid may comprise an electroactive component, such as water, suitable for an electrochemical reaction (such as electrolysis to produce $H_2$ and $O_2$, for example) at the working electrode 104, and may further comprise a component that impedes the electrochemical reaction at the working electrode such that it becomes mass-transport limited.

Still further, merely by way of example, the electrochemical reaction of interest at the working electrode 104 may be a promoted electrochemical reaction. For example, the fluid may comprise a participant in the electrochemical reaction at the working electrode 104 and a component sufficient to promote the electrochemical reaction of interest and to affect it such that it is mass-transport limited. Such a case may be exemplified by a fluid that comprises a drug, such as an insulin preparation that comprises insulin and a reactant ionic species, such as ionic zinc, as described above, and that comprises a component that promotes the reaction of the reactant at the working electrode. In this case, the component is sufficiently dilute relative to the fluid that it causes the electrochemical reaction of interest to be mass-transport limited. For example, the rate of the promoted electrochemical reaction is affected by the dilute concentration of the promoter component of the fluid.

The fluid 202 and the component 204 should be of suitable compatibility with one another. Merely by way of example, a pharmaceutical insulin preparation and an ionic zinc component thereof are generally compatible with one another, such that the preparation is relatively stable, for example. It will be understood that when the fluid is delivered to a flow path that communicates with a living subject or lies within a living subject, the fluid and the component should be of suitable compatibility with one another, and should be of suitable biocompatibility with the living subject when the life of the living subject is to be relatively uncompromised. It will also be understood that the device or any component thereof or any adaptation thereof, and the fluid and the component thereof, should be compatible with one another. Merely by way of example, when the fluid is insulin, which may be inclined to adsorb out of solution onto certain surfaces, the surfaces of the electrodes in the electrochemical cell should be selected to minimize or substantially avoid such adsorption. It will further be understood that when the device is associated with a flow path of a living subject, the device or any component thereof or any adaptation thereof that comes into intimate contact with the living subject should be of suitable biocompatibility with the living subject when the life of the living subject is to be relatively uncompromised. It will be also understood that when the electrochemical reaction takes place within or in intimate contact with a living subject, any product of the electrochemical reaction should be of suitable biocompatibility with the living subject when the life of the living subject is to be relatively uncompromised. Still further, it will be understood that any product of the electrochemical reaction, and the fluid and the component thereof, should be of suitable compatibility with one another.

A temperature of the fluid in the flow path may be taken to provide additional information about the flow condition of the fluid. Thus, the device of the present invention may comprise a temperature probe 112, as shown in FIG. 1, that is sufficient for communication with fluid 202 in the flow path 200. The temperature of the fluid in the flow path may affect mass transport of the component 204 of the fluid to the electrochemical cell. In some cases, the effect of temperature on such mass transport may be fairly minimal, as may be the case in various drug delivery applications, such as the delivery of an insulation preparation that contains ionic zinc. In such cases, information regarding temperature may not be needed or desired. In other cases, the effect of temperature may be more pronounced or significant, such that obtaining information regarding the temperature of the fluid may be desirable or necessary. When temperature information is obtained, it may be used to calibrate or to control the fluid delivery device or pump. Merely by way of example, the temperature reading may be received by a microcontroller (further described herein) and used to correct data concerning a condition of the flow of the fluid accordingly, via an empirically- or a theoretically-based algorithm, for example. Merely by way of example, the algorithm may be used to correct current or voltage data received from the electrochemical cell 102 by some level or percentage for each degree of temperature deviation from a baseline temperature.

A fluid delivery device or pump may not need calibration. Merely by way of example, it may be quite feasible to determine the relationship between a flow of fluid from a fluid delivery device and an indication of a characteristic of that flow that is obtained from a device of the present invention, without calibration. In some cases, such as when the relationship just described cannot be feasibly or adequately determined, it may be desirable or necessary to calibrate a fluid delivery device or pump. Merely by way of example, the manufacture and/or performance of fluid delivery devices or pumps may not be sufficiently reliable or consistent such that the calibration of each manufactured device can feasibly be avoided. Calibration of a fluid delivery device or pump may comprise obtaining an indication of the fluid delivery associated with the fluid delivery device, such as a volume or a flow rate of fluid that flows from the fluid delivery device, for example, and substantially simultaneously, obtaining an indication of a characteristic of that flow of the fluid, such as a current or voltage, for example. The indication of the fluid delivery associated with the fluid delivery device may be obtained using a device or a method of the above-referenced U.S. Patent Application Publication No. 2005/0235732 A1 of Benjamin M. Rush, entitled "Fluid Delivery Device with Autocalibration." The indication of a characteristic of the flow of the fluid may be obtained using a device or a method of the present invention, as described herein. The two indications may be obtained over time, via monitoring, using the first and the second of the above-described devices, respectively, for example.

The information obtained, such as temperature, fluid volume or flow rate, current, voltage, and/or the like, as described above, may be provided to the microprocessor of the device of the present invention for use in the calibration of the fluid delivery device and/or the control of the fluid delivery device. Merely by way of example, the reaction rate associated with a component of the fluid, as may be related to the current or voltage obtained, of a known quantity of fluid, as may be related to the volume obtained, may be used, with or without temperature compensation, as appropriate, to assess a flow condition of the fluid, for use in the calibration and/or the control of the fluid delivery device. Calibration of the fluid delivery device may comprise performing a calibration according to an algorithm that is stored in a microprocessor (further described herein), or the like. Control of the fluid delivery device may comprise providing an indication of proper or improper fluid delivery, which may be based on a predetermined set of limits or a predetermined range that may be stored in a microprocessor (further described herein), such as via a display of information or an alarm, for example, such that a recipient of the information or alarm can adjust the fluid delivery device or the flow of fluid therefrom, or automatically adjusting the fluid delivery device or the flow of fluid therefrom via a feedback loop. A suitable microprocessor, or multiple microprocessors, may handle all of the foregoing. In the case of drug delivery, redundant microprocessors may be used, as may be desirable or required for safety, for example.

A particular embodiment of the present invention is now described. According to this embodiment, a fluid from a fluid delivery pump is delivered to a subject. As shown in FIG. 2, a device 600 comprising an electrochemical cell 102, including a working electrode (WE) 104, a counter electrode (CE) 108, and a reference electrode (RE) 102 is disposed at at least one location in a fluid flow path. The at least one location may include a location that is relatively near the point where the fluid leaves the pump and/or a location that is relatively near the point where the fluid enters the body of the subject. In this embodiment, the electrochemical cell 102 is a micro-electrochemical cell wherein the working area of the working electrode 104 is about 0.1 mm$^2$ or less.

As also shown in FIG. 2, the device 600 comprises at least one microcontroller 500 operably connected to the at least one cell 102 for providing a current or a potential to the working electrode 104 of the cell sufficient for the electrochemical reaction to take place there, and for receiving information concerning the electrochemical reaction, such as the rate of the electrochemical reaction. One such microcontroller 500 may be used in connection with one cell or multiple cells 102. Further, more than one microcontroller 500 may be used in connection with one cell or multiple cells 102. Still further, a microcontroller 500 and a cell 102 may be associated with one another, another microcontroller 500 and another cell 102 may be associated with one another, and so on. Generally, any suitable association of at least one microcontroller 500 and at least one electrochemical cell 102 may be employed. The microcontroller 500 may also be operably connected to a temperature probe 112 for receiving information concerning temperature of the fluid 202, as previously described.

At least one microcontroller 500 of the device 600 is sufficient for providing a potential to the working electrode 104 and for receiving information concerning an electrochemical reaction associated with the electrochemical cell 102. The working electrode potential may be any suitable potential and may be selected from any of a variety of potentials suited to the particular electrochemical reaction contemplated and/or suited to the particular reference electrode contemplated, merely by way of example. The microcontroller 500 may be sufficient for providing an indication related to a current or charge associated with the electrochemical reaction, or an assessment of a change in the electrochemical reaction rate, by way of example. Merely by way of example, when the fluid 202 is delivered to the flow path 200 in at least two pulses, the at least one microcontroller 500 of the device 600 is sufficient for providing a current or a potential to the working electrode 104 to facilitate the electrochemical reaction and for assessing the electrochemical reaction associated with each of the at least two pulses, and/or with the at least two pulses at a predetermined interval, such as every few minutes, for example. The microcontroller 500 may be operably associated with a display device, a recording device, a printing device, and/or any device sufficient for communicating information concerning the electrochemical reaction and/or temperature. The microcontroller 500 may be operably connected with the pump 400 for feedback control, such as to adjust a pumping parameter such as flow volume, flow rate, pulse frequency, or pulse duration, merely by way of example, based on information concerning the flow condition and/or temperature of the fluid 202 in the flow path 200.

In an example of the use of this embodiment of the device 600, the fluid in the flow path is an insulin preparation that contains a dilute ionic zinc component, namely, ionic zinc. A pharmaceutical insulin preparation often contains ionic zinc (for example, from ZnCl), which happens to be suitable for electrochemical reaction ($Zn^+ + e^- \rightarrow Zn$) at the electrochemical cell. In this example, the insulin preparation is delivered via the flow path in consecutive doses, in between which there is an absence of flow. When a dose of the insulation preparation is delivered and the ionic zinc component thereof first reaches the electrochemical cell, the rate of electrochemical reaction at the electrochemical cell, which may be measured as a current, is initially that associated with the bulk (maximum) concentration of the ionic zinc in the fluid. Thereafter, the rate of electrochemical reaction at the electrochemical cell, as reflected by current, for example, will begin to diminish, as ionic zinc in the vicinity of the electrochemical cell is consumed, such that ionic zinc must diffuse to the electrochemical cell from further and still further points upstream. When a new dose of the insulation preparation is delivered and the ionic zinc component thereof first reaches the electrochemical cell, the rate of reaction, as reflected by current, for example, will return to that associated with the bulk concentration of the ionic zinc in the fluid. The above-described diminishment and return of the rate of reaction, or current signal, may occur quite rapidly.

A functional model of the above-described device of the present invention was constructed and tested according to the above-described example. A flow path was constructed out of a length of Teflon tubing with ID of 0.0625 of an inch. The electrochemical cell comprised a carbon counter electrode and an Ag/AgCl reference electrode both screen-printed on plastic film, and a gold wire working electrode of 0.010 of an inch in diameter. The electrodes were inserted into the Teflon tube by drilling a small hole in the side of the tube and sealing the electrodes in place with epoxy. A pharmaceutical insulin preparation (U100 Humalog from Eli Lilly (Indianapolis, Ind.)), containing ionic zinc at a concentration of 0.0003 M, was delivered through the flow path in a pulsed manner, with a pulse volume of approximately 2 µLs and a pulse period of 235 seconds. The electrode potential was held at −0.6V versus the Ag/AgCl reference electrode in an attempt to reduce $Zn^+$ ion to Zn metal on the surface of the gold working electrode.

Figure 3:
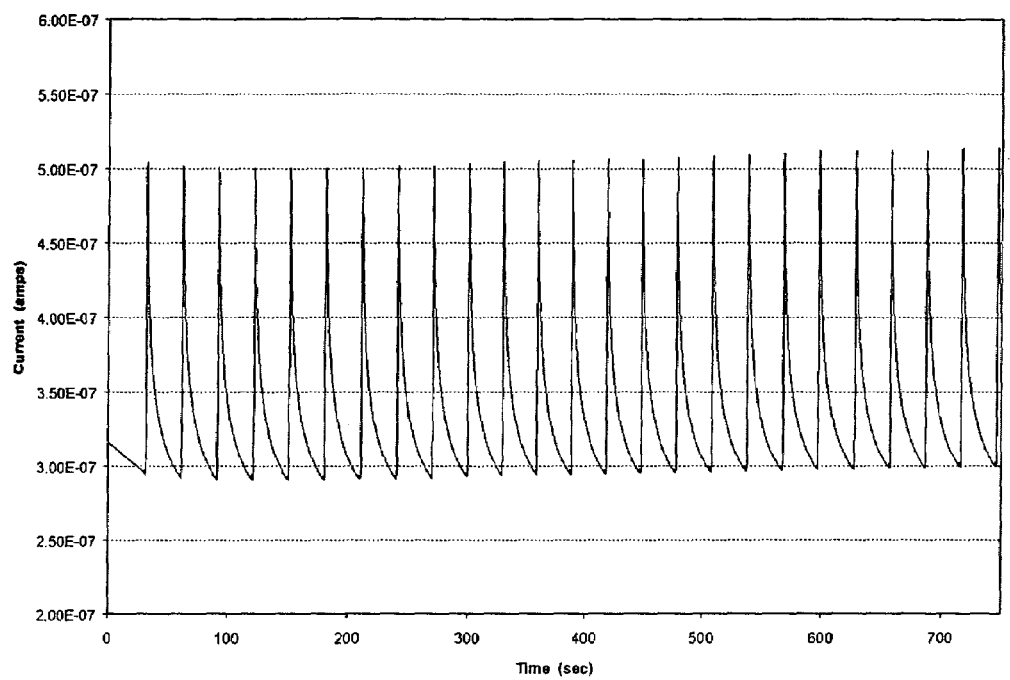
FIG. 3 (FIG. 3) is a graphical representation of current (amperes) versus time (seconds) associated with an example concerning a device according to an embodiment of the present invention.

The current associated with the electrochemical reaction at the electrochemical cell was recorded during the pulsed delivery of the insulin preparation through the flow channel, as shown in FIG. 3. Each pulse of fluid delivered from the pump corresponded with a distinct current pulse of large amplitude, as illustrated by the current peaks shown in FIG. 3. The data obtained may be assessed qualitatively and/or qualitatively.

Figure 4:
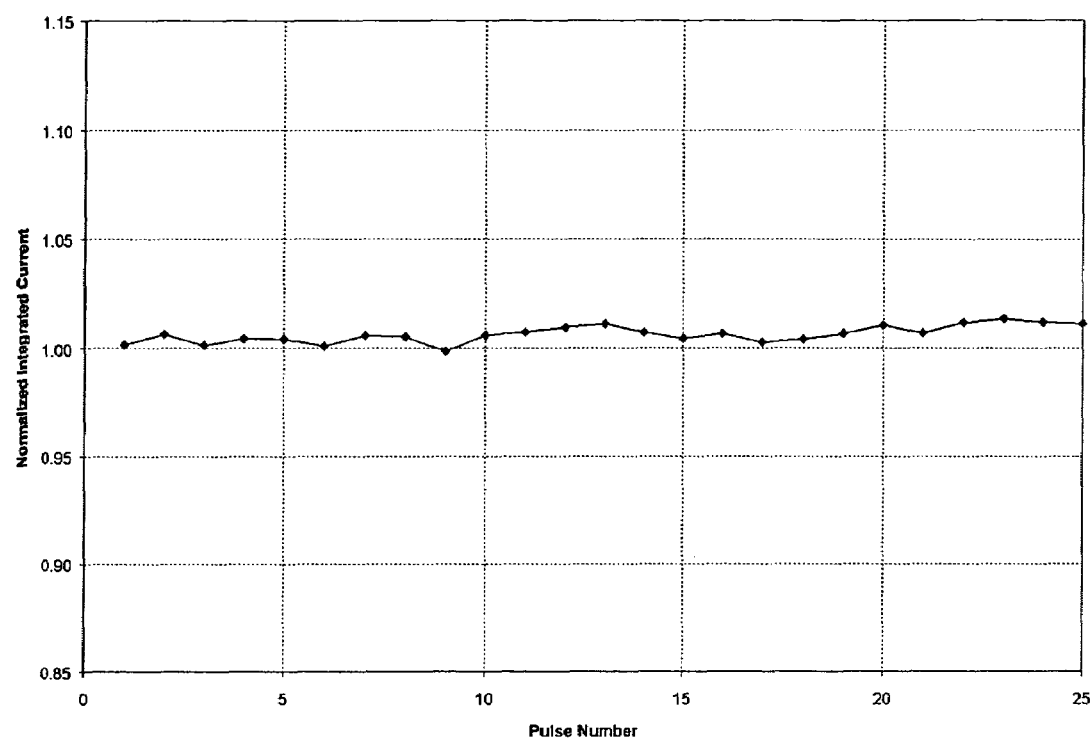
FIG. 4 (FIG. 4) is a graphical representation of a normalized integration of the current pulses versus pulse number associated with an example concerning a device according to an embodiment of the present invention.

By way of example, the area of under the curve associated with each current pulse shown in FIG. 3, or the integral of each current pulse, can be viewed and an assessment can be made as to whether the areas or integrals appear to be the same or substantially the same on a qualitative basis, as is the case in FIG. 3, or not. Further by way of example, the integral of each current pulse shown in FIG. 3 can be determined, as shown in FIG. 4, and an assessment can be made as to whether the integrals are the same or substantially the same on a quantitative basis, as is the case in FIG. 4, or not. Any suitable means or method may be used to assess the data, be it human, machine, automated, and/or otherwise.

Figure 5:
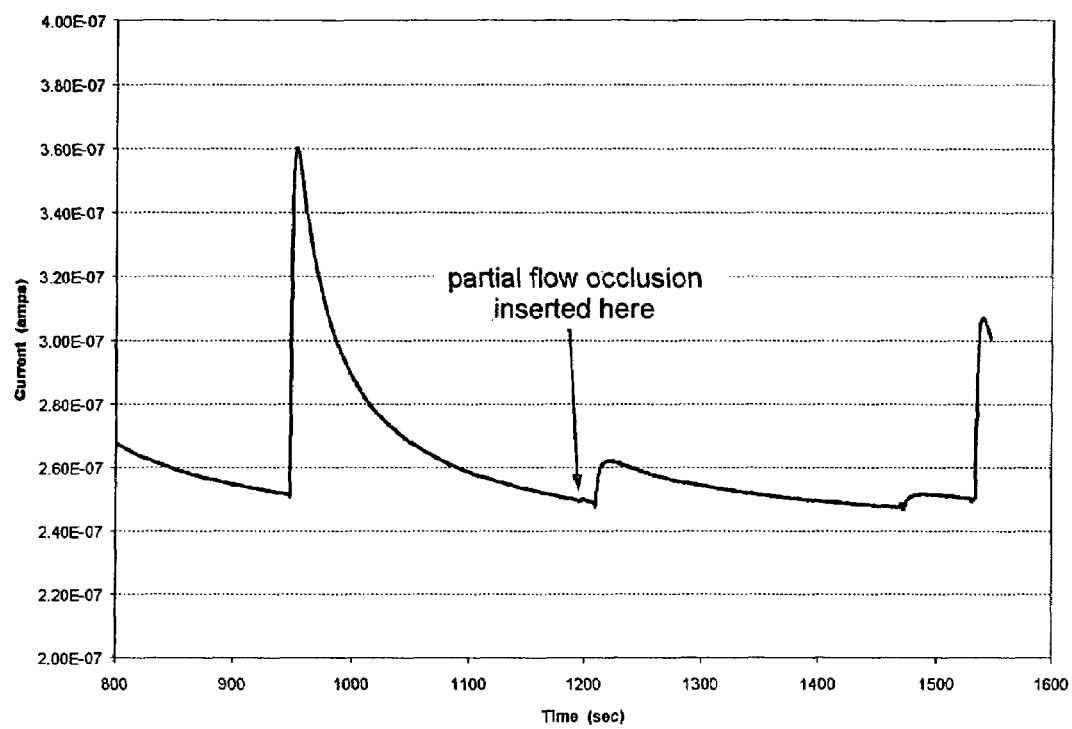
FIG. 5 (FIG. 5) is a graphical representation of current (amperes) versus time (seconds) associated with an example concerning a device according to an embodiment of the present invention.

The functional model just described was also tested as described above, with the exception that the pulsed delivery of the insulin preparation was unrestricted and then partially restricted by compressing the Teflon tubing at the end upstream relative to the electrochemical cell. Each pulse of fluid delivered from the pump in this manner corresponded with a distinct current pulse, as shown in FIG. 5. The first peak, corresponding to a pulse of fluid from the unrestricted tube, is of significant amplitude, while the second peak, corresponding to a pulse of fluid from the restricted tube, is of relatively reduced amplitude. A test involving compressing the Teflon tubing at different points, whether upstream or downstream relative to the electrochemical cell, could also be undertaken, and would be expected to give similar results regardless of the location of the restriction. Further, it is believed, although this was not tested, that if the pump in the above-described embodiment were to fail such that a continuous flow of insulin was delivered, a continuous current value corresponding to that of the peak amplitudes of the current pulses shown in FIG. 3 would result. In this manner, the device of the present invention may be used to detect insufficient fluid flow from a pump, such as an insulin pump, and/or to detect excessive fluid flow from a pump, in a qualitative and/or quantitative manner.

Any of the devices and methods described herein may be used to assess, measure, and/or monitor the flow of any fluid that comprises, or has added to it, an electrochemically reactive component, such as a dilute electrochemically reactive component, for example. Any such devices and methods may be used to assess, measure, and/or monitor such flow of any magnitude and of any flow characteristic, such as a type of flow, such as continuous or non-continuous flow, for example, an example of the latter being pulsed flow, a direction of flow, a current or force associated with or influencing flow, and the like, and any combination thereof. Merely by way of example, any such devices and methods may be used to assess, measure, and/or monitor pulsed flow to ascertain whether or not each pulse of fluid has a suitable volume, such as whether or not such each pulse of fluid is of substantially the same volume, for example. Any such devices and methods may be used to assess, measure, and/or monitor an impediment to a desirable or an intended delivery of fluid, such as by way of a gaseous bubble, such as an air bubble, for example, that interferes with such delivery (for example, the bubble displaces the fluid so that the delivery of the fluid is less than what would otherwise be delivered). The presence of such a bubble may significantly affect an indicator associated with the electrochemical cell, such as current, for example, such as reducing the current significantly or to zero. This may be useful in assessing whether such a bubble is present in the flow path of, or from, a fluid delivery device, for example.

Any such devices and methods are particularly well suited to flow of a small scale, such as the flow of a liquid drug from an automatic portable drug delivery device to a subject. Examples of such drug delivery devices and methods, and the flow associated therewith, include those of the above-referenced U.S. Pat. No. 6,916,159 and U.S. Patent Application Publication No. 2005/0238503 A1 of Benjamin Rush et al., which may be calibrated according to the devices and methods of the above-referenced U.S. Patent Application Publication no. 2005/0235732 A1 of Benjamin M. Rush, merely by way of example. Further, any such devices and methods may be used in connection with an automatic portable drug delivery device, which in turn, may be associated with an implantable device, such as an implantable sensing device that is used to sense an analyte, such as glucose, within a subject, such as a diabetic subject. Examples of such implantable devices, and associated methods, include those of several U.S. Patent Nos. and U.S. Patent Application Publication Nos., as follows: U.S. Pat. No. 6,175,752 of Say et al., filed on Apr. 30, 1998; U.S. Pat. No. 6,329,161 of Heller et al., filed on Sep. 22, 2000; U.S. Pat. No. 6,560,471 of Heller et al., filed on Jan. 2, 2001; U.S. Pat. No. 6,579,690 of Bonnecaze et al., filed on Jul. 24, 2000; U.S. Pat. No. 6,654,625 of Say et al., filed on Jun. 16, 2000; U.S. Pat. No. 6,514,718 of Heller et al., filed on Nov. 29, 2001; U.S. Pat. No. 6,605,200 of Mao et al., filed on Nov. 14, 2000; U.S. Pat. No. 6,605,201 of Mao et al., filed on Nov. 14, 2000; 6,932,894 of Mao et al., filed on May 14, 2002; 2005/0173245 A1 of Feldman et al., filed on Apr. 6, 2004; and 2005/0215871 A1 of Feldman et al., filed on Dec. 7, 2004, for example, each of which is hereby incorporated herein, in its entirety, by this reference.

Any of the devices and methods described herein may be used to assess, measure, and/or monitor the flow of any liquid that comprises, or has added to it, a dilute electrochemically reactive component, in a qualitative and/or quantitative manner. In a qualitative assessment, a general observation of the presence or absence of a current signal, or the amplitude of a current signal, may be used to assess flow condition, merely by way of example. In a quantitative or semi-quantitative assessment, the presence or absence of a current signal, or the amplitude of a current signal or the integral of a current peak, or a portion thereof, may be used to assess flow condition, merely by way of example. An assessment of a current signal or a charge generated, such as a charge generated in connection with electrolysis, may be obtained by any suitable means, such as amperometry or coulometry, merely by way of example.

An assessment of flow condition that is obtained via any of the devices and methods of the present invention may be used as a basis for adjusting the flow of the fluid in the flow path, or adjusting a device, such as a pump, that generates the flow of the fluid in the flow path, by any suitable means or methods. Such an adjustment may comprise any of those described in the above-referenced U.S. Pat. No. 6,582,393 and U.S. Patent Application Publication No. 2004/0019321 A1. Merely by way of example, when the fluid in the flow path is delivered in a pulsed manner, such as via discrete periodic pulses of nominally identical volumes of fluid, and an assessment of the flow condition shows the pulse volume to be 5% larger than the nominal volume, the pulse period may be decreased by 5% so as to reestablish the intended overall flow condition, or delivery rate, or some other fluid delivery or pulse parameter may be controlled or changed to obtain desirable results. Further by way of example, when the fluid in the flow path is delivered in a continuous manner, such as in a continuous flow via gravity or via pressure from a source of fluid, such as a reservoir or a bladder, that is controlled, such as via opening or closing or adjusting of a control device, such as a valve, and an assessment of the flow condition shows the flow volume or rate to be 5% smaller than the nominal volume, the control device may be adjusted so as to increase the flow volume or rate to obtain suitable or desirable results.

The microcontroller of the device of the present invention may comprise any appropriate elements or components for achieving any of its intended purposes. Examples of such elements or components include any one or more of the following: electronic circuitry, componentry, storage media, signal- or data-processing elements, algorithmic elements, software elements, logic devices, wired or wireless communication elements, devices for operable communication between elements or components, and the like. Examples of such intended purposes include any one or more of the following: providing a potential or a current to a working electrode, obtaining information from the electrochemical cell, obtaining information from a fluid delivery device, obtaining information from a temperature probe, obtaining information pertinent to calibration and/or control of a fluid delivery device, assessing or processing any obtained or internal information, communicating with the electrochemical cell or another device, such as a fluid delivery device, a display device, an alarm or notification device (sensory or otherwise), and/or a calibration device, such as an autocalibration device, communicating via a feedback loop, such as an automated feedback loop, and calibrating and/or controlling another device, such as a fluid delivery device. A microcontroller may be configured to include any suitable elements described herein, or any suitable elements for achieving any of the purposes described herein, in a conventional manner. Any device with which the microcontroller may communicate may be equipped with complementary elements, such as any suitable communication elements, components, or devices, such as wired or wireless communication elements, merely by way of example, as may be afforded or accomplished in a conventional manner.

Any of the devices or methods of the present invention may be suited or adapted to be suited for use in connection with an electrochemical reaction at the electrochemical cell that is continuous or intermittent. Merely by way of example, the working electrode of the cell may be biased in order to start an electrochemical reaction at the electrochemical cell prior to an anticipated pulse of fluid flow and to terminate the electrochemical reaction at some time after the pulse of fluid flow. Further by way of example, an electrochemical reaction at the electrochemical cell may be assessed, measured, and/or monitored in connection with every pulse of fluid flow, or in connection with one or more pulse(s) of fluid flow at some regular interval, such as at every hour or at every hundredth pulse, as may be useful in terms of optimizing or reducing consumption of a battery and/or other power source (not shown) associated with the pump or the device of the invention, optimizing or extending the life of the electrodes of the device of the invention, minimizing consumption of the component of the fluid, and/or minimizing production of one or more reaction product(s), for example.

As previously described, any of the devices or methods of the present invention can be used in connection with a fluid delivery device such as a pump. According to a preferred embodiment, as now described, a device or method of the present invention may be used in connection with a fluid delivery device, or pump, that has automatic calibration and/or control capability. Information concerning the construction and the operation of such a fluid delivery device may be found in the above-referenced U.S. Patent Application Publication No. 2005/0235732 A1 of Benjamin M. Rush filed concurrently herewith.

Figure 6A:
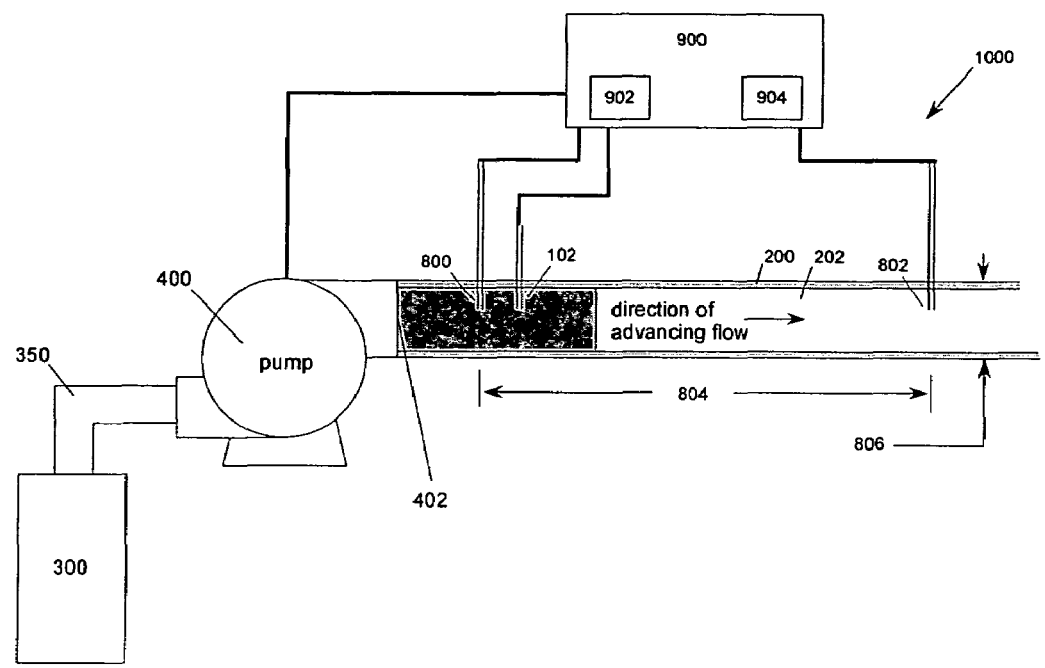
FIG. 6A (FIG. 6A) is a schematic illustration of a device according to an embodiment of the present invention. Each of FIG. 6B (FIG. 6B) and FIG. 6C (FIG. 6C), independently, is a schematic illustration, in the form of a flow chart, of a method according to an embodiment of the present invention.
Figure 6B:
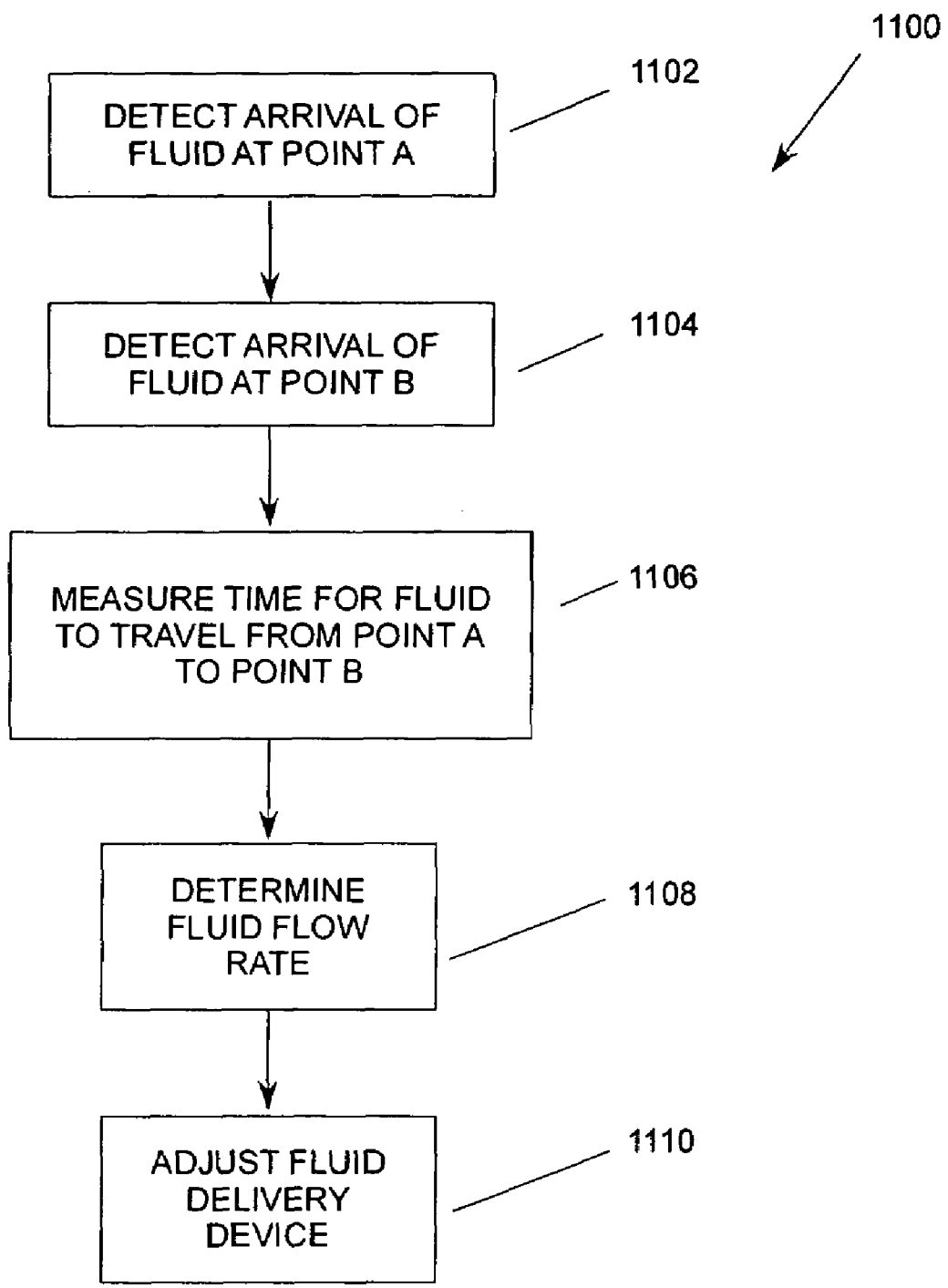

A schematic illustration of a device 1000 that may comprise or be used in association with a fluid delivery device 700, is shown in FIG. 6A, and a flow chart describing the operation of such a fluid delivery device 700 is shown in FIG. 6B. The fluid delivery device 700 may be of any suitable type, such as a fluid pump, for delivery of a fluid from an outlet thereof to a flow path 202. It may be preferable to use a fluid pump that is driven by a shape memory actuator in certain cases, for example, when cost is a driving factor or when the device is used in connection with applications, such as medical applications, in which devices may be disposed of and replaced relatively frequently for various reasons. Information concerning the construction and the operation of such a fluid delivery device may be found in the above-referenced U.S. Pat. No. 6,916,159 and the above-referenced U.S. Patent Application Publication No. 2005/0238503 A1 of Benjamin Rush et al. filed concurrently herewith. The fluid delivery device 700 may comprise or be used in association with a user interface (not shown) for setting one or more operating parameter(s), such as a fluid delivery rate, an activation or deactivation of the fluid delivery device, and the like, and any combination thereof.

According to a preferred embodiment, the fluid delivery device has automatic calibration and/or control capability, as now described in connection with the device 1000 shown in FIG. 6A. The device 1000 comprises at least two sensors, an upstream sensor 800, and a downstream sensor 802 that are in communication with the flow path 200. This communication may be similar to that associated with the electrochemical cell 102, as previously described. Each of the sensors comprises a pair of conductive electrodes. The electrodes may be made of a material suitable for a particular application. Merely by way of example, when the fluid to be delivered is an insulin solution, gold or gold-plated electrodes may be used. A current and/or a voltage passing between the electrodes of the pair, and/or a charge and/or a resistance associated with the electrode pair, may indicate the presence of a fluid that has at least some measure of electrical conductivity (such as an insulin preparation that contains ionic zinc, for example) at the electrodes. Thus, an indication of current, voltage, charge, and/or resistance, such as zero current, voltage, charge, and/or resistance, versus some amount of current, voltage, charge, and/or resistance, from an electrode pair may be detected and used to indicate the absence or presence of a fluid at the electrodes. Any of the electrode pairs just described is typically used to provide a qualitative measure of the existence or non-existence of fluid, based on the existence or non-existence of electrical continuity in the electrode pair circuit.

It will be understood that any of the electrode-pairs may be employed as part of an electrochemical cell if a quantitative measure is desired, although this may be more complicated than is desirable or necessary where a simple indication of existence or non-existence of fluid is desired. Further, it will be understood that a flow-monitoring electrode may serve as a current-sensing electrode, and that a current-sensing electrode may serve as a flow-monitoring electrode.

The volume of the flow path between the two sensors, or the calibration region 708, is known or ascertainable. Merely by way of example, when the distance 704 between the two sensors and the diameter 706 of the flow path 200 are known, the volume of the flow path between the two sensors, or of the calibration region 708, can be determined or known. It will be understood that while the flow path 200 may be cylindrical, as depicted in FIG. 6A, merely by way of example, such that the volume associated with the calibration region 708 may be determined or known in the manner just described, the flow path 200 may be of any geometric (regular or irregular) shape or configuration, such that the volume associated with the calibration region 708 may be otherwise known or ascertainable. It may be desirable to have the volume of the calibration region 708 much greater than the volume of fluid to be delivered in the flow path. Merely by way of example, when the fluid to be delivered is an insulin solution, the volume of the calibration region 708 is preferably much greater than the volume of an individual dose of insulin solution to facilitate good resolution and accuracy in the detection or measurement of the flow rate or the current.

The two sensors 800 and 802 and the fluid delivery device 700 are connected to a control unit 900. The control unit 900 comprises drive circuitry 902 and logic unit 904, which is preferably in the form of a microcontroller or microprocessor, such as that previously described in connection with FIG. 2. The control unit 900 may be used for the general control of the fluid delivery device 700 and its operation. The control unit 900 may also be used to initiate and control calibration of the fluid delivery device 700.

Control 1100 of the fluid delivery device 700 may proceed as depicted in FIG. 6B, merely by way of example. Such a control process 1100 may be performed at any time. Merely by way of example, such a process 1100 may be carried out in conjunction with priming the fluid delivery device 700. The control 1100 comprises the detection 1102 of the arrival of fluid at a point A, which corresponds to a location of the up-stream sensor 800. The detection 1102 may be via the control unit 900 described above. In association with this detection 1102, the flow stream may be allowed to advance to the upstream sensor 800 or may be interrupted before it reaches the upstream sensor 800. Merely by way of example, the flow may be interrupted via the introduction of a gas bubble into the flow stream. The control 1100 also comprises the detection 1104 of the arrival of fluid at a point B, which corresponds to a location of the downstream sensor 802. The detection 1104 may be via the control unit 900 described above.

The control 1100 also comprises the determination 1106 or measurement of the time it takes for the fluid to travel from point A to point B. The determination 1106 may be via the control unit 900 described above. As described previously, the volume of the flow path in the calibration region 808 is known or ascertainable. Data concerning this volume may be entered via a user interface (not shown) and/or stored in memory in the control unit 900. The control 1100 also comprises determining 1108 or calculating the flow rate associated with the fluid, such as a volumetric flow rate, based on these time and volume parameters. The determination 1108 may be via the control unit 900 described above.

The control 1100 may comprise the adjustment 1110 of the fluid delivery device 700, or the fluid flow therefrom, based on the fluid flow rate, or no adjustment of the fluid delivery device 700 where such is undesirable or unnecessary. The adjustment 1110 may comprise providing the fluid flow rate to a user, who could then adjust the pump, if and as may be appropriate, such as via a user interface (not shown), in any appropriate manner, or automatically adjusting the pump, such as via an automated feedback loop, in any appropriate manner. Control 1100 of the fluid delivery device 700 may take place at any suitable time, such as before or at the time fluid delivery from the device 700 commences, or at any time during fluid delivery from the device 700. Further information concerning control of a fluid delivery device may be found in the above-referenced U.S. Patent Application Publication No. 2005/0235732 A1 of Benjamin M. Rush filed concurrently herewith.

Figure 6C:
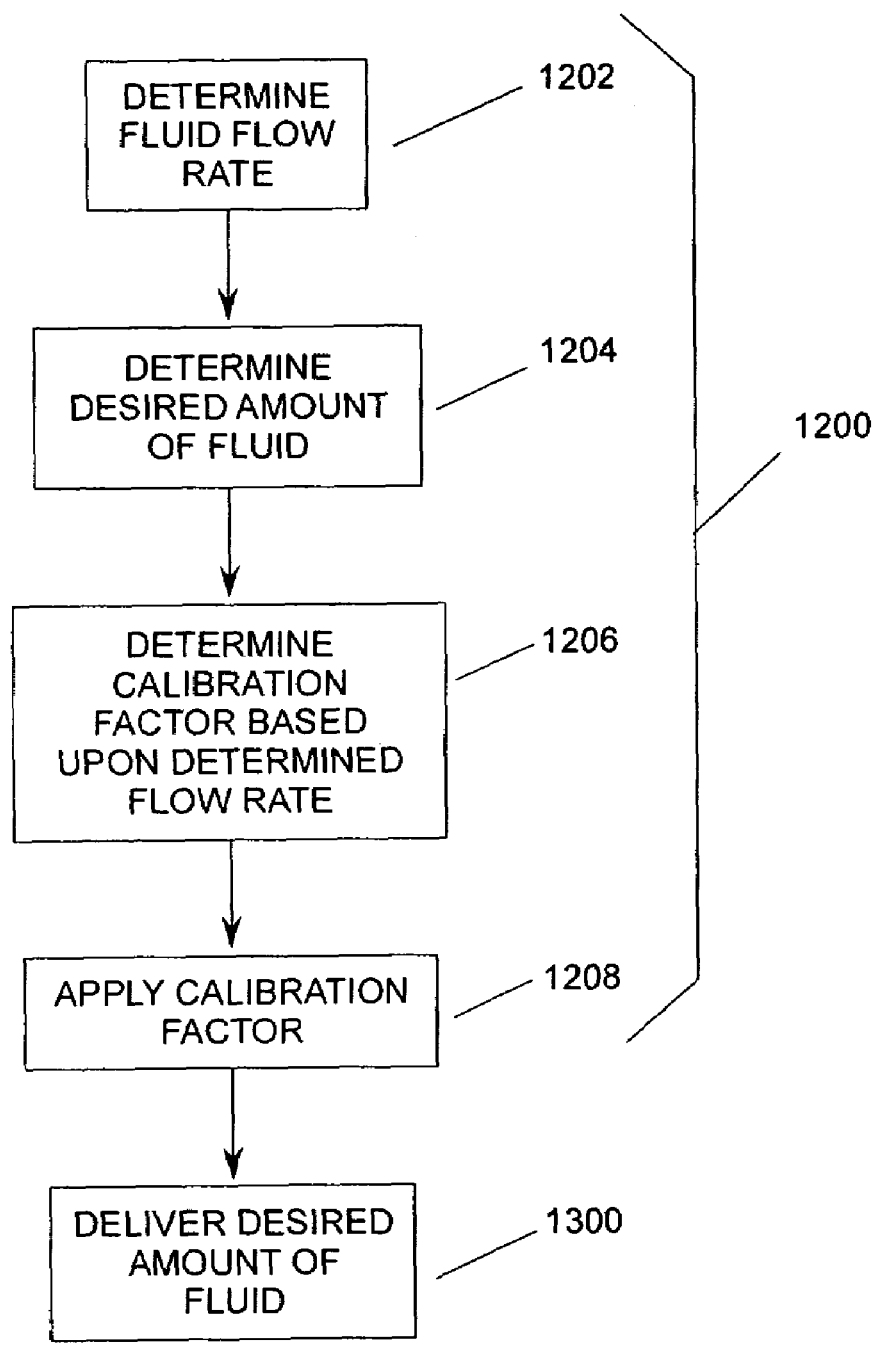

Calibration 1200 of the fluid delivery device 700 may proceed as depicted in FIG. 6C, merely by way of example. Such a calibration process 1200 may be performed at any time. The calibration 1200 comprises determining 1202 a fluid flow rate, such as a volumetric flow rate, which may be performed as described previously in relation to FIG. 6B. The determination 1202 may be via the control unit 900 described above. The calibration 1200 may comprise determining 1204 a suitable or desirable fluid delivery amount, such as a volume or a dose volume, for example, or a suitable or desirable fluid delivery rate. This volume or rate may be known. Data concerning the volume or rate may be entered via a user interface (not shown) and/or stored in memory in the control unit 900. The determination 1204 may be via the control unit 900 described above.

The calibration 1200 also comprises determining 1206 a calibration factor based on this determined fluid flow rate. The calibration factor may, and preferably does, comprise a ratio of an expected or nominal amount or volume of fluid to be delivered, such as a dose volume, for example, and an actual volume of fluid delivery delivered. The determination 1206 may be via the control unit 900 described above. The calibration 1200 also comprises applying 1208 the calibration factor in connection with operation of the fluid delivery device 700, such as in connection with delivering a suitable or desirable amount or volume of fluid, such as a dose, from the fluid delivery device. The application 1208 of the calibration factor may be via the control unit 900 described above.

The calibration factor may be applied 1208 in connection with an adjustment of the fluid delivery device 700, if desirable or necessary, which may be performed as described previously in relation to FIG. 6B. The calibration 1200 may comprise the adjustment of the fluid deliver device 700 based on the determined fluid flow rate and/or the calibration factor, or no adjustment of the fluid delivery device 700 where such is undesirable or unnecessary. The adjustment may comprise providing the determined fluid flow rate and/or calibration factor to a user, who could then adjust the fluid delivery device, if and as may be appropriate, in any appropriate manner, or automatically adjusting the fluid delivery device, such as via an automated feedback loop, in any appropriate manner. Calibration 1200 of the fluid delivery device 700 may take place at any suitable time, such as before or at the time fluid delivery from the device 700 commences, or at any time during fluid delivery from the device 700. Further information concerning calibration of a fluid delivery device may be found in the above-referenced U.S. Patent Application Publication No. 2005/0235732 A1 of Benjamin M. Rush filed concurrently herewith. Preferably, a suitable or desirable amount or volume of fluid, such as a dose, is delivered 1300, from the fluid delivery device 700, whether or not an actual adjustment of the device is performed, as also shown in FIG. 6C.

According to the present invention, a device and a method for assessing a flow condition of a fluid are provided. The device and the method are drawn from more or less discrete disciplines, such as the disciplines of electrochemistry, micro-fluidics, mass transport, kinetics, fluid pumping, fluid flow, pulsed flow, pump monitoring, and flow measurement, merely by way of example. Although each of these disciplines has its own nuances and complexities, the device and the method of the present invention may be rather simple and inexpensive and may provide useful qualitative and/or quantitative assessments of the flow condition of a fluid.

According to a preferred embodiment, the device and the method of the present invention may have useful application in the delivery of a drug or medicament to a subject, such as the automated delivery of such a drug or medicament to a subject, and more particularly, the precise automated delivery of such a drug or medicament to a subject, with optional feedback control, such as automated feedback control. It is contemplated that the present invention may be used in connection with an analyte-sensing device, such as an implantable analyte-sensing device, and an associated drug delivery device that is provided in a patch that may be worn by a subject, such as an adhesive patch that may be affixed to the skin of a subject. Merely by way of example, the present invention may be used in connection with any of the devices and methods disclosed in U.S. Provisional Patent Application No. 60/664,215 of Benjamin Rush et al., entitled "Method and Apparatus for Providing Integrated Infusion Device and Monitoring System," filed on Mar. 21, 2005, which is hereby incorporated herein, in its entirety, by this reference. Further, merely by way of example, the analyte-sensing device may comprise a glucose-sensing device, the drug delivery device may comprise an insulin delivery device, the subject may be afflicted with diabetes, and the device and method may be associated with a flow channel of the drug delivery device, a natural flow channel of the subject, or any suitable flow path, as described herein. Still further, merely by way of example, the present invention may be used in connection with any of the devices and methods associated with an in vivo FreeStyle® Navigator™ glucose monitoring device (Abbott Diabetes Care, formerly known as TheraSense, Inc., of Alamada, Calif.), that is currently in clinical trials, though not now commercially available, and is based on or related to several of the above-referenced U.S. patents and patent applications, namely, U.S. Pat. Nos. 6,175,752, 6,329,161, 6,560,471, 6,579,690, 6,654,625, 6,514,718, 6,605,200, 6,605,201, and 6,932,894, and U.S. Patent Application Publication Nos. 2005/0173245 A1 and 2005/0215871 A1, for example.

Figure 7:
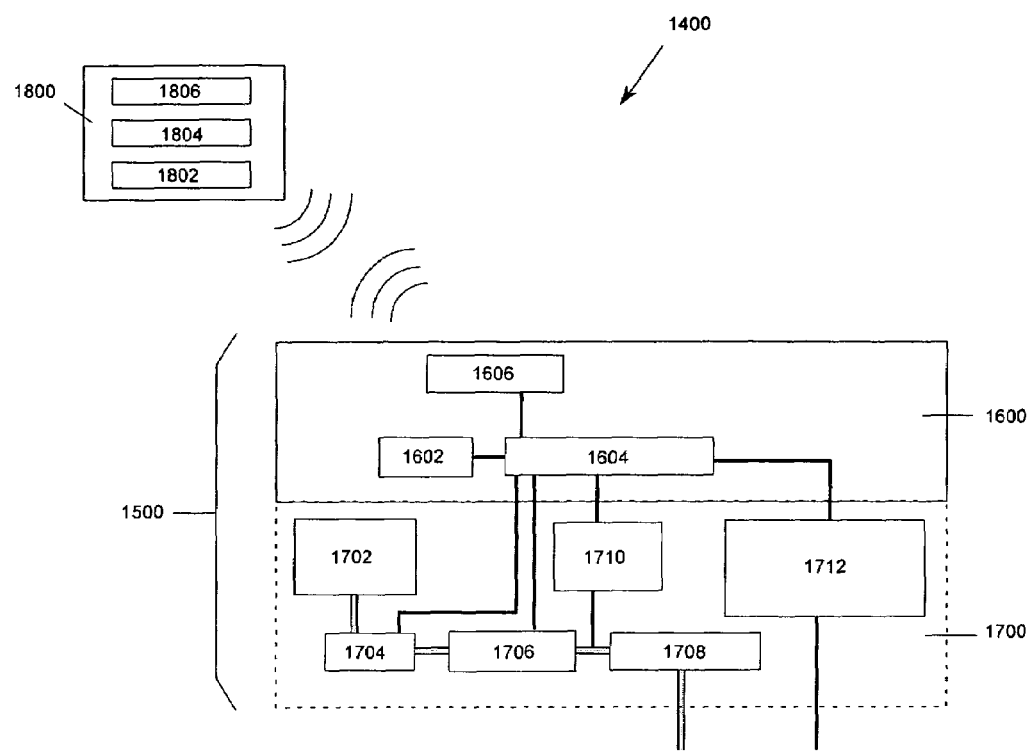
FIG. 7 (FIG. 7) is a schematic illustration of a system according to an embodiment of the present invention.

According to a preferred embodiment of the present invention, a system 1400 as shown in FIG. 7 is provided. The system 1400 comprises a patch 1500 that may be used on a portion of a subject's body (not shown). The patch 1500 may be appended or attached to the portion of the subject's body in any suitable manner, such as via adhesive that adheres to the skin of the subject, merely by way of example. The patch may comprise a portion 1600 (shown with solid outline), which may be reusable, and another portion 1700 (shown in broken outline), which may be disposable. The patch 1500 may house a number of components, such as any of the components shown in FIG. 7, and any combination thereof.

The portion 1600 comprises a battery 1602 and a microcontroller 1604, such as any of same previously described. The portion 1600 may also comprise a transceiver 1606 for the communication of information, which may be a wired transceiver (not shown) or a wireless transceiver suitable for communication with a remote unit 1800 or a transceiver 1802 thereof, such as via signals, for example, as represented by arced lines. The portion 1700 comprises a fluid reservoir 1702, such as an insulin reservoir, a fluid delivery device 1704, such as a pump, a calibration device 1706, which may be a calibration device as previously described, an infusion set 1708, a flow measurement or monitoring device 1710, which may be such a device as previously described, and a continuous analyte-sensing device 1712, such as a continuous blood glucose-monitoring device as previously described. An infusion set generally refers to a device that connects a fluid delivery device to subcutaneous tissue of a subject, which may comprise a piece of tubing having a luer connection or lock on one end for connection to the fluid delivery device and a needle or soft flexible plastic tube on the other end for insertion into the subcutaneous tissue, merely by way of example, at least part of which may be associated with a patch, such as an adhesive patch that secures at least the insertion needle or tube in place, for example. An infusion set is typically a disposable device that is replaced periodically, such as every three or so days.

It will be understood that the solid lines between any two components of the patch 1500, as shown in FIG. 7, represent any suitable method or device for operable communication between those components. Further, it will be understood that the two solid lines with a grey or shaded interior between any two components of the patch 1500, as shown in FIG. 7, or from the infusion set 1708 of the patch 1500, represent any suitable method or device for operable fluid communication between those components, or from the infusion set, respectively.

As mentioned above, a remote unit 1800 may be used in connection with the patch 1500. This may be a remote, hand-held or easily portable unit. The remote unit 1800 comprises a transceiver 1802 for the communication of information, which may be a wired transceiver (not shown) or a wireless transceiver suitable for communication with a patch 1500 or a transceiver 1606 thereof, such as via signals, for example, as represented by arced lines. The remote unit 1800 may also comprise a user interface 1804 for receiving information from a user, for communicating information (such as flow parameter (rate, pulse, duration, etc.) instructions or adjustments, for example) from a user to the fluid delivery device 1704, and/or for communicating information to the user. The remote unit also comprises a data storage device for storing data, such as any data received from the patch 1500 and/or any data received from the user interface 1804. Any appropriate operable connections between the components of the remote unit 1800 may be used.

The system 1400 may be used for delivery of a fluid to a subject, for calibration associated with such delivery, for control associated with such delivery, for communication of information associated with such delivery, for fluid delivery based on information from a continuous analyte-sensing device, automated fluid delivery, automated fluid delivery control, automated fluid delivery calibration, automated feedback fluid delivery based on information from a continuous analyte-sensing device, and/or the like, as will be understood from the description herein. Preferably, the micro-controller 1604 is sufficient for facilitating or carrying out any or all of these various functions. The system 1400 may be used for any such applications in a convenient manner, in that the system 1400 may be small, compact, partially disposable, partially reusable, relatively low in energy consumption, relatively convenient in communication, such as wireless communication, and/or the like, merely by way of example.

According to another embodiment of the present invention, a transient electric double-layer charging current may be used to measure or monitor fluid flow. By way of explanation, when an electrode is immersed into an electrolyte, an accumulation of ions from the electrolyte forms spontaneously at the electrode surface as a result of the disturbance in the electrical environment of the ions that is caused by the electrode. The accumulation of ions consists of a layer of ions adsorbed directly on the electrode surface and a diffuse arrangement of ions in the electrolyte just off the surface of the electrode. Accordingly, this accumulation of ions is known as the electric double layer. When the electric double layer is initially forming, a transient current will flow through the electrode as mobile charges in the electrode adjust to the new electrical environment of the electrolyte. The arrangement of ions in the double layer is a function of the potential of the electrode and will change if the potential or current, respectively, of the electrode is changed. This potential-dependent structure of ions in the double layer will also generate a transient current if the potential of the electrode is changed.

Furthermore, flow of the electrolyte near the electrode can disturb the ions in the diffuse layer of ions which will generate a transient current as the diffuse layer of ions are reordered. Measurement of this transient current can be used as a measure and/or monitor of fluid flow. The electric double layer may be associated with any of numerous electrochemical phenomena, such as double-layer charging, electrochemical capacitance, electrophoresis, and electroosmosis.

As to methods of the present invention, a method of assessing a flow condition of a fluid is disclosed herein. Such a method comprising providing a fluid sufficient to support an electrochemical reaction at a working electrode of an electrochemical cell, wherein the fluid comprises a component sufficient to affect the electrochemical reaction such that the electrochemical reaction is mass-transport limited. Such a method further comprises providing at least one electrochemical cell comprising the working electrode and at least one other electrode in communication with the fluid and obtaining an indicator of a rate of the electrochemical reaction. As previously described, the method may comprise adjusting a parameter of the flow of the fluid, as may be done in view of the indicator obtained, for example.

Another method of assessing a flow condition of a fluid is also provided. Such a method comprises providing a flow path for the fluid described above and/or a source of fluid in communication with such a flow path for delivering the fluid to the flow path. In this method, the fluid may be provided continuously or non-continuously, such as in at least two pulses. In the latter case, such a method may comprise obtaining an indicator of the rate of the electrochemical reaction associated with the at least one electrochemical cell and associated with each of at least two pulses, such as doing so at a predetermined interval, for example. As previously described, the indication may be related to a current, a potential, a charge, or any combination thereof, associated with the electrochemical reaction. The method may further comprise feedback control of the source of fluid, such as feedback control based on the indication obtained, as previously described herein.

Various devices, systems, and methods have been described herein. It will be understood that a method of use or application is naturally contemplated in connection with any device or system described herein, and a device or system for carrying out a method is naturally contemplated in connection with any method described herein.

It will be appreciated that each of the device and the method of the present invention has many useful medical applications, as well a wide variety of other useful applications that involve the flow of fluid. Merely by way of example, any of various aspects that affect the performance of a flow assessment, measurement, and/or monitoring device of the present invention, could be assessed, measured, and/or monitored, in cases where other aspects of such performance are known and/or constant. Such aspects include reactant concentration, temperature, fluid viscosity, and laminar flow velocity distribution, merely by way of example.

Various modifications, processes, as well as numerous structures to which the present invention may be applicable will be readily apparent to those of skill in the art to which the present invention is directed, upon review of the specification. Various references, publications, provisional and/or non-provisional United States or foreign patent applications, and/or United States or foreign patents, have been identified herein, each of which is hereby incorporated herein, in its entirety, by this reference. Various aspects and/or features of the present invention have been explained or described herein in relation to understandings, beliefs, theories, underlying assumptions, and/or working or prophetic examples, although it will be understood that the invention is not bound to any particular understanding, belief, theory, underlying assumption, and/or working or prophetic example. Although the various aspects and features of the present invention have been described with respect to various embodiments and specific examples herein, it will be understood that the invention is entitled to protection within the full scope of the appended claims.

The invention claimed is:

1. A method of assessing a flow condition of a fluid, comprising:
   determining a time period associated with a delivery of a fluid, the fluid comprising a component to support an electrochemical reaction such that the electrochemical reaction is mass-transport limited;
   monitoring a rate of electrochemical reaction in a fluid path of the fluid delivery for the determined time period; and
   determining a rate of the fluid delivery based at least in part on the monitored rate of electrochemical reaction;
   wherein the fluid comprises a drug and the component comprises a reactant in the electrochemical reaction that is dilute relative to the fluid, and the reactant is an ionic species.

2. The method of claim 1, wherein the fluid comprises a material selected from insulin, an antibiotic, a nutrient, a dietary supplement, a health supplement, total parental nutrition, an analgesic, an anesthetic, a pain reliever, a hormone, a hormonal drug, a gene therapy drug, an anticoagulant, a cardiovascular drug, AZT, a chemotherapeutic drug, any source thereof, or any combination thereof.

3. The method of claim 1, wherein the component is of a concentration of from about $10^{-7}$M to about $10^{-2}$M relative to the fluid.

4. The method of claim 1, wherein the fluid is insulin and the reactant is ionic zinc.

5. The method of claim 1, wherein the fluid delivery is provided in a continuous manner.

6. The method of claim 1, wherein the fluid delivery is provided in a non-continuous manner.

7. The method of claim 1, wherein the fluid delivery is provided in at least two pulses.

8. The method of claim 7, wherein the monitored rate of electrochemical reaction is associated with each of the at least two pulses.

9. The method of claim 7, wherein the monitored rate of electrochemical reaction is associated with the at least two pulses at a predetermined interval.

10. The method of claim 1, wherein monitored rate of electrochemical reaction includes a current, a potential, a charge, or any combination thereof.

11. The method of claim 1, further comprising calibrating the rate of the fluid delivery based at least in part on the monitored electrochemical reaction.

12. The method of claim 1, further comprising controlling the rate of the fluid delivery based at least in part on the monitored electrochemical reaction.

13. The method of claim 12, wherein the controlling is automated.

14. The method of claim 1, further comprising obtaining a temperature of the fluid.

15. The method of claim 14, further comprising controlling the rate of the fluid delivery based at least in part on the temperature.

16. The method of claim 15, wherein the controlling is automated.

17. The method of claim 1 wherein the component at least in part interferes with transport of the reactant.

18. A method of assessing a flow condition of a fluid, comprising:
   determining a time period associated with a delivery of a fluid, the fluid comprising a component to support an electrochemical reaction such that the electrochemical reaction is mass-transport limited;
   monitoring a rate of electrochemical reaction in a fluid path of the fluid delivery for the determined time period; and
   determining a rate of the fluid delivery based at least in part on the monitored rate of electrochemical reaction;
   wherein the fluid comprises a drug and the component comprises a reactant in the electrochemical reaction that is dilute relative to the fluid, and the drug is insulin and the reactant is ionic zinc.

19. The method of claim 18, wherein the component is of a concentration of from about $10^{-7}$M to about $10^{-2}$M relative to the fluid.

20. The method of claim 18, wherein the fluid delivery is provided in a continuous manner.

21. The method of claim 18, wherein the fluid delivery is provided in a non-continuous manner.

22. The method of claim 18, wherein the fluid delivery is provided in at least two pulses.

23. The method of claim 22, wherein the monitored rate of electrochemical reaction is associated with each of the at least two pulses.

24. The method of claim 22, wherein the monitored rate of electrochemical reaction is associated with the at least two pulses at a predetermined interval.

25. The method of claim 18, wherein monitored rate of electrochemical reaction includes a current, a potential, a charge, or any combination thereof.

26. The method of claim 18, further comprising calibrating the rate of the fluid delivery based at least in part on the monitored electrochemical reaction.

27. The method of claim 18, comprising controlling the rate of the fluid delivery based at least in part on the monitored electrochemical reaction.

28. The method of claim 27, wherein the controlling is automated.

29. The method of claim 18, comprising obtaining a temperature of the fluid.

30. The method of claim 29, comprising controlling the rate of the fluid delivery based at least in part on the temperature.

31. The method of claim 30, wherein the controlling is automated.

32. A method of assessing a flow condition of a fluid, comprising:
   determining a time period associated with a delivery of a fluid, the fluid comprising a component to support an electrochemical reaction such that the electrochemical reaction is mass-transport limited;
   monitoring a rate of electrochemical reaction in a fluid path of the fluid delivery for the determined time period; and
   determining a rate of the fluid delivery based at least in part on the monitored rate of electrochemical reaction;
   wherein the fluid comprises a reactant in the electrochemical reaction and the component at least in part interferes with transport of the reactant, and the fluid comprises a drug and the reactant is an ionic species.

33. The method of claim 32, wherein the fluid comprises a material selected from insulin, an antibiotic, a nutrient, a dietary supplement, a health supplement, total parental nutrition, an analgesic, an anesthetic, a pain reliever, a hormone, a hormonal drug, a gene therapy drug, an anticoagulant, a cardiovascular drug, AZT, a chemotherapeutic drug, any source thereof, or any combination thereof.

34. The method of claim 32, wherein the component is of a concentration of from about $10^{-7}$M to about $10^{-2}$M relative to the fluid.

35. The method of claim 32, wherein the fluid is insulin.

36. The method of claim 32, wherein the drug is insulin and the reactant is ionic zinc.

37. The method of claim 32, wherein the fluid delivery is provided in a continuous manner.

38. The method of claim 32, wherein the fluid delivery is provided in a non-continuous manner.

39. The method of claim 32, wherein the fluid delivery is provided in at least two pulses.

40. The method of claim 39, wherein the monitored rate of electrochemical reaction is associated with each of the at least two pulses.

41. The method of claim 39, wherein the monitored rate of electrochemical reaction is associated with the at least two pulses at a predetermined interval.

42. The method of claim 32, wherein monitored rate of electrochemical reaction includes a current, a potential, a charge, or any combination thereof.

43. The method of claim 32, comprising calibrating the rate of the fluid delivery based at least in part on the monitored electrochemical reaction.

44. The method of claim 32, comprising controlling the rate of the fluid delivery based at least in part on the monitored electrochemical reaction.

45. The method of claim 44, wherein the controlling is automated.

46. The method of claim 32, comprising obtaining a temperature of the fluid.

47. The method of claim 46, comprising controlling the rate of the fluid delivery based at least in part on the temperature.

48. The method of claim 47, wherein the controlling is automated.

49. The method of claim 32 wherein the component is dilute relative to the fluid.

50. A method of assessing a flow condition of a fluid, comprising:
    determining a time period associated with a delivery of a fluid, the fluid comprising a component to support an electrochemical reaction such that the electrochemical reaction is mass-transport limited;
    monitoring a rate of electrochemical reaction in a fluid path of the fluid delivery for the determined time period; and
    determining a rate of the fluid delivery based at least in part on the monitored rate of electrochemical reaction;
    wherein the fluid comprises a reactant in the electrochemical reaction and the component at least in part interferes with transport of the reactant, and the fluid comprises insulin and the reactant is ionic zinc.

51. The method of claim 50 wherein the component is dilute relative to the fluid.

52. The method of claim 50, wherein the component is of a concentration of from about $10^{-7}$M to about $10^{-2}$M relative to the fluid.

53. The method of claim 50, wherein the fluid delivery is provided in a continuous manner.

54. The method of claim 50, wherein the fluid delivery is provided in a non-continuous manner.

55. The method of claim 50, wherein the fluid delivery is provided in at least two pulses.

56. The method of claim 55, wherein the monitored rate of electrochemical reaction is associated with each of the at least two pulses.

57. The method of claim 55, wherein the monitored rate of electrochemical reaction is associated with the at least two pulses at a predetermined interval.

58. The method of claim 50, wherein monitored rate of electrochemical reaction includes a current, a potential, a charge, or any combination thereof.

59. The method of claim 50, comprising calibrating the rate of the fluid delivery based at least in part on the monitored electrochemical reaction.

60. The method of claim 50, comprising controlling the rate of the fluid delivery based at least in part on the monitored electrochemical reaction.

61. The method of claim 60, wherein the controlling is automated.

62. The method of claim 50, comprising obtaining a temperature of the fluid.

63. The method of claim 62, comprising controlling the rate of the fluid delivery based at least in part on the temperature.

64. The method of claim 63, wherein the controlling is automated.

* * * * *